(12) United States Patent
Rönngren (10) Patent No.: US 12,366,916 B2
(45) Date of Patent: Jul. 22, 2025

(54) METHOD AND SYSTEM FOR DETERMINING A CURRENT GAZE DIRECTION

(71) Applicant: Tobii AB, Danderyd (SE)

(72) Inventor: Denny Rönngren, Danderyd (SE)

(73) Assignee: Tobii AB, Danderyd (SE)

( * ) Notice: Subject to any disclaimer, the term of this patent is extended or adjusted under 35 U.S.C. 154(b) by 112 days.

(21) Appl. No.: 18/146,215

(22) Filed: Dec. 23, 2022

(65) Prior Publication Data

US 2023/0214011 A1    Jul. 6, 2023

(30) Foreign Application Priority Data

Dec. 30, 2021 (SE) .................... 2151638-0

(51) Int. Cl.
*G06T 19/20* (2011.01)
*G06F 3/01* (2006.01)
(Continued)

(52) U.S. Cl.
CPC .............. *G06F 3/013* (2013.01); *G06T 19/20* (2013.01); *G06T 2219/2016* (2013.01)

(58) Field of Classification Search
CPC .................. G06T 19/006; G06T 19/20; G06T 2219/2016; G06T 2207/30201; G06T 15/205; G06T 15/50; G06T 15/20; G06T 15/06; G06T 7/246; G06T 2200/04; G05D 1/0263; G05D 1/0027; G05D 1/0244;
(Continued)

(56) References Cited

U.S. PATENT DOCUMENTS 10,216,268 B2 *  2/2019  Lindh ................. G06F 3/013
10,579,142 B2 *  3/2020  Lindh ................. G05D 1/0242
(Continued)

FOREIGN PATENT DOCUMENTS

CN    111949131 A    11/2020
WO    20210167704 A1    8/2021

OTHER PUBLICATIONS

European Search Report for EP Appl. Nr. 22216859.1, completed on May 12, 2023, 2 pages.
(Continued)

*Primary Examiner* — Wesner Sajous
(74) *Attorney, Agent, or Firm* — Christopher Ignatius Moylan (57) ABSTRACT

Method for determining a current gaze direction of a user in relation to a three-dimensional ("3D") scene, the 3D scene being sampled by a rendering function to produce at least one projection image of the 3D scene, wherein the method comprises the steps: determining, by a reprojection means, a reprojection transformation to be applied to the projection image before being displayed so as to be visible to the user at a gaze time point; determining, by a gaze direction detection means, a physical gaze direction of the user at said gaze time point; and determining a modified gaze direction of the user at said gaze time point, the modified gaze direction being determined in relation to the 3D scene based on both the physical gaze direction and the reprojection transformation. The disclosure also relates to a system and to a computer software function.

15 Claims, 4 Drawing Sheets

(51) Int. Cl.
*G06T 15/20* (2011.01)
*G06V 20/64* (2022.01)

(58) Field of Classification Search
CPC ........... G05D 1/0242; G06F 3/011–013; G06F 3/017; G06F 3/034815; G06V 40/193; G06V 20/64; G02B 27/01; A63F 13/52
See application file for complete search history.

(56) References Cited

U.S. PATENT DOCUMENTS

| | | | |
|---|---|---|---|
| 11,032,534 B1* | 6/2021 | Voss-Wolff | G06T 17/20 |
| 2016/0267708 A1 | 9/2016 | Nistico et al. | |
| 2017/0372457 A1 | 12/2017 | Sylvan et al. | |
| 2018/0227630 A1 | 8/2018 | Schmidt et al. | |
| 2018/0300943 A1* | 10/2018 | Lindh | G06T 15/20 |
| 2018/0365882 A1 | 12/2018 | Croxford et al. | |
| 2020/0125312 A1 | 4/2020 | Ohashi | |
| 2020/0241635 A1 | 7/2020 | Cohen | |
| 2020/0278746 A1* | 9/2020 | Lindh | G06F 3/013 |
| 2020/0285311 A1* | 9/2020 | Lindh | G05D 1/0242 |
| 2021/0011549 A1* | 1/2021 | Ryan | G02B 27/0172 |
| 2021/0012559 A1* | 1/2021 | Lindh | G06T 15/50 |
| 2021/0067765 A1* | 3/2021 | Beeler | H04N 13/363 |
| 2022/0130107 A1* | 4/2022 | Lindh | G02B 27/01 |

OTHER PUBLICATIONS

SE2151638-0, "Search Report", Sep. 16, 2022, 8 pages.
Chinese Office Action for CN 202211685541.3, completed on Aug. 28, 2024.

* cited by examiner

METHOD AND SYSTEM FOR DETERMINING A CURRENT GAZE DIRECTION

CROSS-REFERENCES TO RELATED APPLICATIONS

The present application claims priority to Swedish patent application No. 2151638-0, filed Dec. 30, 2021, entitled "Method and system for determining a current gaze direction", and is hereby incorporated by reference in its entirety for all purposes.

TECHNICAL FIELD

The present invention relates to a method for determining a current gaze direction of a user in relation to a three-dimensional ("3D") scene. The invention also relates to a system and to a computer software function for performing such a method.

Embodiments of the present invention relate to tracking a user's gaze when the user is observing a 3D scene, and in particular how to determine a point, zone or entity to which a user's gaze is currently directed in the 3D scene.

BACKGROUND OF THE INVENTION

It is known to detect an eye and its gaze direction. This can be done, for example, by illuminating a region in which the eye is sought with infrared radiation; capturing an image of the region; and detecting bright spots in the image that derive from the pupil and cornea of the eye. This approach exploits the bright-eye or "red-eye" effect known to photographers, whereby light enters the eye and is reflected or absorbed and re-emitted through the pupil, making the pupil appear brighter than the rest of the eye and the face. A separate, smaller bright spot (also referred to as a glint) is created by the cornea. The relative positions of the pupil and the corneal glint can be used to determine the direction of the gaze of the eye. More details are given in U.S. Pat. No. 6,152,563.

Alternatively, or in addition thereto, a similar technique may be used whereby infrared illuminators are spaced from an image sensor, thus an image captured by the image sensor has a non-bright pupil, otherwise known as a "dark pupil" effect.

This gaze tracking technology may be implemented in a remote gaze tracker located adjacent a display for example, or in a wearable device such as a pair of glasses, a virtual reality headset, an augmented reality headset, a helmet or the like.

Such gaze tracking technology can be used to determine if a user is looking at a particular object or an area on a screen (these objects or areas are generically referred to as 'zones' in the present application). This could be as part of a game, for example, allowing users to interact with images on a screen by looking at them (the act of looking at the image having a predetermined result) or by a combination of looking at an image and another control (e.g., a user pressing a key on a keyboard or mouse whilst their gaze is directed at the image).

When determining where in relation to a 3D scene the gaze of a user is currently directed, consideration must be taken to the physical gaze direction of the user, in relation to a physical viewing region such as a screen. However, consideration must also be taken to the current state of the scene itself, and to the virtual camera's current virtual 3D space position and direction. This is true both for 2D and 3D scenes.

Herein, a "simulated" scene means a scene the final presentation or appearance of which results from some type of computer simulation of a defined virtual model. The final presentation in question is in the form of a 2D image (such as a bitmap on a screen display) or a 3D image (such as a hologram). The "simulation" in question happens before the rendering of the final presentation, and comprises taking into consideration dynamic properties of the scene, such as mutable objects present in the scene and/or geometric transformations of the defined virtual model itself (in virtual space) in relation to a defined viewpoint of a user. Typically, such "simulation" takes into consideration certain predefined rules, that may form part of the definition of said virtual model, regarding how such mutations will progress over time in an at least partly, or at least statistically, deterministic manner based on such rules.

It has turned out that, due to various latencies, the user experience will typically be less than perfect in, for example, dynamic game situations where all these parameters may change quickly.

A first type of situation occurs when, for instance, a user watches a particular object in a virtual 3D scene as shown on a monitor screen. The watched object is then present at a particular location on the said screen. Then, the virtual camera used to render the 3D scene into the 2D image viewed on the screen is rotated and/or translated, and as a result the viewed 2D image changes correspondingly. However, because of latency, the gaze point of the user on the said screen will remain the same until the user's eyes have reacted to the virtual camera shift, by the user moving her gaze so as to again focus on the said object, which has previously moved as a result of the virtual camera shift. Thereafter, hardware latency results in a time delay before the game controller (or similar) detects the changed user gaze point on the screen, so that a user interaction function can react appropriately.

In a second type of situation, the 3D scene changes in itself, such as by the said object moving through the virtual 3D scene, whereby similar latency effects will result even if the virtual camera position or direction does not change.

US 2020/278746 A1 presents a solution that works for these first and second types of situations, by determining a virtual camera 3D transformation between a time when a gaze direction is determined by measurements and a time when a next frame is rendered, and then determining an adjusted gaze direction using a reverse of that 3D transformation.

However, this solution requires knowledge of a dynamic state of a virtual camera used to render the scene in question.

In a third type of situation, the scene is first rendered, using a virtual camera, resulting in a presentation of the above type. Then, however, the rendered presentation is reprojected, in a separate process provided downstream of the renderer. Such a reprojection is a transformation applied to the rendered 2D or 3D image to be presented to the user before actually being shown. For instance, reprojections can be used to quickly be able to react to a user moving or turning her head when wearing a head posture-sensitive VR/AR monitor, (head-mounted display, HMD); to account of frames missed by the renderer due to GPU shortfalls; adjustments due to lens properties; and so forth. For such reprojections, the scene is not rendered anew to produce the reprojected presentation, but instead the already rendered image is transformed by applying a transformation to the rendered presentation as a whole. It may also be the case that the same rendered image is presented at different time points using different reprojections/movement adjustment. This may for instance be the case when images are produced at a lower frame frequency then a desired finally output frame frequency.

In this third type of situation, even if the gaze detecting mechanism has access to information regarding the dynamic properties of a virtual camera used to perform the rendering, the reprojection takes place downstream of such rendering. Still, similar problems as in the first and second types of situations may arise as a result of said reprojections.

These problems result not only in a poorer user experience, but also limit the time-wise granularity with which a user interaction with the 3D scene can be implemented.

Particular problems arise for GTOM (Gaze To Object Mapping) implementations, in which a system attempts to detect a stationary or movable object on the screen as a currently focused object which the user fixates on or follows with her gaze.

Typically, gaze detection algorithms may use various buffers, herein collectively referred to as "tag buffers", being simplified or scope-restricted representations of various scene properties such as depth, colour and geometrical features. For instance a depth buffer and a stencil buffer are both tag buffers in the present sense. One such tag buffer may be a gaze interaction mask. The use of such tag buffers in determining a user gaze direction is described in US 2016/0357255 A1. When a gaze direction is determined in relation to a rendered scene based on information contained in one or several such tag buffers, the determined gaze direction will in general become uncertain or invalid upon a reprojection of the presentation.

These problems may be partially overcome by providing faster hardware and more efficient software. However, this is expensive and doesn't solve all of the problems.

Hence, the present invention aims to at least partially overcome the problems described above.

BRIEF SUMMARY OF THE INVENTION

Hence, the invention relates to a method for determining a current gaze direction of a user in relation to a three-dimensional ("3D") scene, the 3D scene being sampled by a rendering function to produce at least one projection image of the 3D scene, wherein the method comprises the steps: determining by a reprojection means, a reprojection transformation to be applied to the projection image before being displayed so as to be visible to the user at a gaze time point; determining, by a gaze direction detection means, a physical gaze direction of the user at said gaze time point; and determining a modified gaze direction of the user at said gaze time point, the modified gaze direction being determined in relation to the 3D scene based on both the physical gaze direction and the reprojection transformation.

Furthermore, the invention relates to a system for determining a current gaze direction of a user in relation to a three-dimensional scene, the 3D scene being sampled by a rendering function to produce at least one projection image of the 3D scene, the system comprising: a gaze direction detection means, arranged to determine a physical gaze direction of the user at a gaze time point; and a modified gaze direction detecting means, arranged to receive information regarding a reprojection transformation applied to the projection image before being displayed so as to be visible to the user at said gaze time point, and further arranged to determine a modified gaze direction of the user at said gaze time point, the modified gaze direction being determined in relation to the 3D scene based on both said physical gaze direction and said reprojection transformation.

Moreover, the invention relates to a computer software function for determining a current gaze direction of a user in relation to a three-dimensional scene, the 3D scene being sampled by a rendering function to produce at least one projection image of the 3D scene, the computer software function configured to, when executed on computer hardware, perform the steps: determine or receive a physical gaze direction of the user at said gaze time point; receive information regarding a reprojection transformation applied to the projection image before being displayed so as to be visible to the user at a gaze time point; and determine a modified gaze direction of the user at said gaze time point, the modified gaze direction being determined in relation to the 3D scene based on both said physical gaze direction and said reprojection transformation.

In the following, the invention will be described in detail, with reference to exemplifying embodiments of the invention and to the enclosed drawings, wherein:

BRIEF DESCRIPTION OF THE DRAWINGS

In all Figures, same reference numerals refer to same or similar parts.

DETAILED DESCRIPTION OF THE INVENTION

The present invention relates to gaze tracking with respect to a 3D scene. The term gaze tracking is used herein to refer to any method or system that detects and/or monitors the location of an eye and/or the direction of the gaze of an eye. The skilled reader will be aware of and understand such systems.

It is also noted that the description also refers to "gaze-interactable" objects or zones. This phrase is intended to indicate objects that the system can detect a user's gaze being directed towards. This may or may not lead to an overt "interaction" for the user. For example, the user may see no sign when a system detects their gaze being directed at a gaze-interactable object. However, the fact that the object has been looked at will have been detected and may be used by the system (e.g., for statistical analysis) in a non-overt manner. Therefore, the term "gaze-interactable" should not be interpreted to require an overt interaction with the user.

Figure 1:
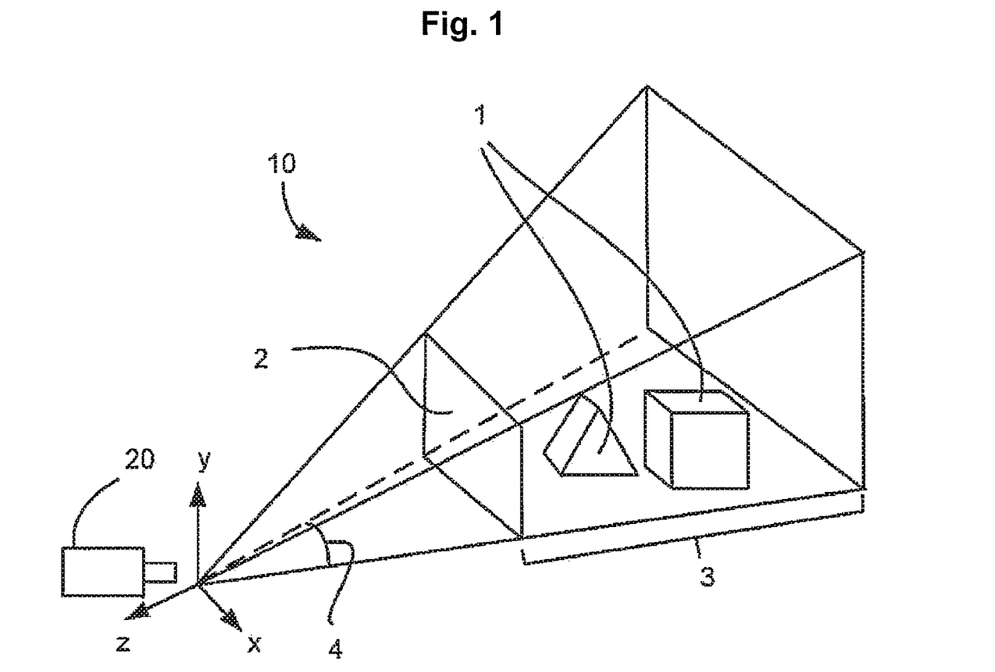
FIG. 1 is a diagram for explaining how a 3D scene is rendered as a 2D image.

FIG. 1 provides an example of a 3D scene 10. Such a scene can be a virtual 3D scene, such as in a computer game or created for a virtual reality headset. The scene 10 contains 3D objects 1. Such objects 1 may move within the scene 10 over time. Indeed, the objects 1 may also move out of the scene 10 and other objects 1 may move into the scene. When such 3D scenes are viewed on a monitor or computer screen, the monitor or screen presents a 2D image representing a view on the 3D scene from a particular location in space, through a viewport 2. The viewport 2 delimits the image that would be seen by a virtual camera 20 or eye located at a notional position with respect to the 3D scene 10. The combination of the position of the virtual camera 20 and the viewport 2 sets the field of view 4. FIG. 1 also shows the view frustum 3, which is the region of the 3D scene 10 (i.e., extending to the rearmost part of the 3D scene 10) that is shown in the viewport 2.

The FIG. 1 diagram also applies to stereoscopic images, such as used in virtual reality headsets for example. In that case, each eye of a user is presented with a slightly different viewport 2 onto a scene 10, from which the user's brain then perceives a single 3D image. See FIG. 3 for an example. In this case each image is usually deformed in a non-linear fashion to compensate for lens characteristics. However, the underlying concepts are the same as discussed with reference to FIG. 1 for each image presented to each of the user's eye.

Figure 2:
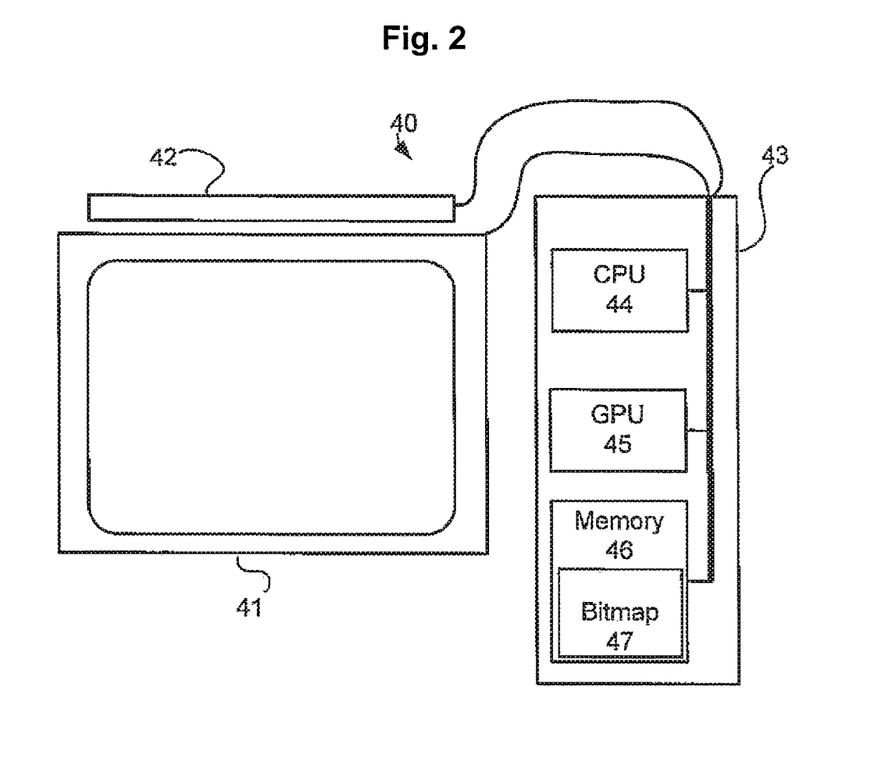
FIG. 2 is a diagram of an exemplifying system for implementing gaze detection.

The 3D objects 1 may be notionally infinitely complex 3D shapes, constructed from polygons. The image viewed via the viewport 2 is a 2D projection of the 3D objects 1 onto the plane of the viewport 2 as seen from the position of the virtual camera 20, as discussed above. However, the screens on which the 2D viewport 2 images are displayed are composed of arrays of discrete elements or pixels. As such, the projections of the 3D objects 1 must be rasterized onto a display grid, by sampling the projected image at each of the screen pixel locations, to produce the image that will be presented as the visual scene (i.e., the scene observed through the viewport 2). The pixel values are stored in a memory area or buffer, as a 2D "bitmap" corresponding to the same dimensions as the screen or viewport 2.

Herein, such rasterization is herein generally denoted a "sampling" of the 3D scene. The sampling is performed by a rendering function, so as to produce said 2D projection image of the 3D scene 10, and is performed by the rendering function based on, inter alia, properties of the virtual camera 20. Such properties of the virtual camera 20, in turn, may comprise a position of the virtual camera 20 and a direction of the virtual camera 20 in relation to the virtual 3D scene 10 in question. In other words, the virtual camera 20 is located at a particular point in virtual 3D space, and is directed in a particular virtual 3D space direction. The rasterized 2D image will depend on both the contents of the virtual 3D scene, as well as on the said camera 20 position and direction.

It is noted that the term "bitmap" has a number of possible meanings. In the context of the present invention, and as is common in the field of computer graphics, it is used to refer to the concept of a spatially mapped array of pixels, which can also be known as a "pixmap". The term bitmap is not intended to convey any limitation in terms of the bit depth of the stored information. In the present invention, the bit depth of the stored information can be variable.

FIG. 2 shows a schematic view of a system 40 according to the present invention, in which the said gaze-detection may be implemented. The system 40 includes a display device, screen or monitor 41 and a gaze-detector (a gaze tracker or gaze direction detection means) 42. The screen 41 may take a conventional or non-conventional form, including a virtual screen such as a retinal projector or a heads-up display in a vehicle. Both the gaze direction detection means 42 and the screen 41 are connected to a computer 43. In modern computers 43, the graphical processing unit (GPU) 45 is often 10-100 times faster than the central processing unit (CPU) 44 for parallelizable computations. As such, it is preferable to implement the present invention using the GPU 45. However, the invention could be implemented using any suitable processor such as a CPU 44.

The computer 43 further comprises a memory 46 into which the said 2D image can be stored as a bitmap 47, and a computer bus as is conventional as such. It is understood that the example shown in FIG. 2 is only for illustration. In practise, the setup may vary, for instance by the gaze-detector 42 being an integrated part of the display device 41 and/or the computer 43.

Figure 3:
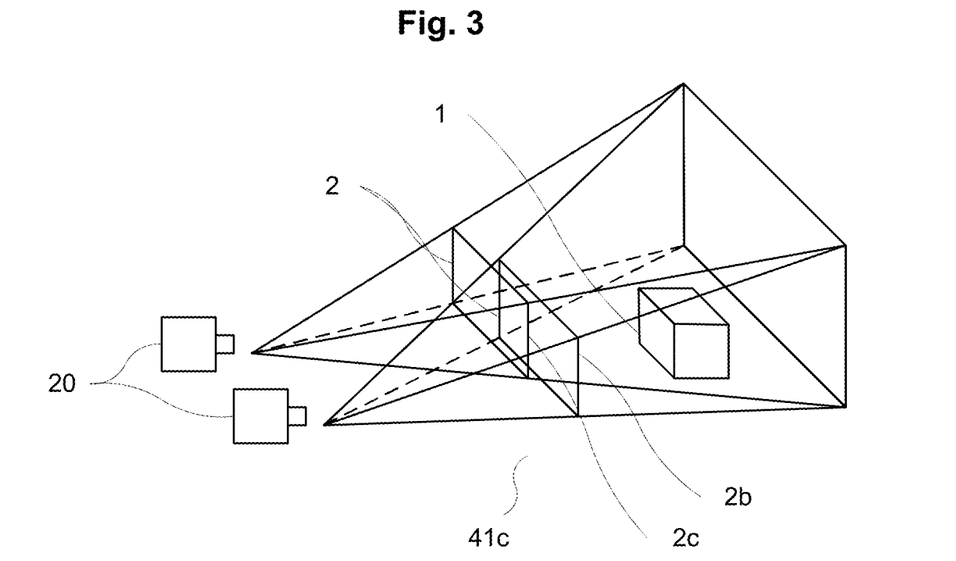
FIG. 3 is a diagram for explaining the operating principal of a stereoscopic image device.

FIG. 3 is a simplified view, being similar to FIG. 1, showing the case where a display device 41*c* is arranged to display a stereoscopic pair of projection images 2*a*, 2*b* in parallel, such as on two different physical display screens, to achieve an immersive AR (Augmented Reality) or VR (Virtual Reality) experience to a user. The user may, for instance, wear the device 41*c* as a head-mounted display unit on her head, the head-mounted display unit comprising said screens and being configured to show a respective one of said projection images 2*a*, 2*b* to each eye of the user in question. One possible position of the display screens of the device 41*c* is at the shown location of the two respective viewports 2.

Figure 4:
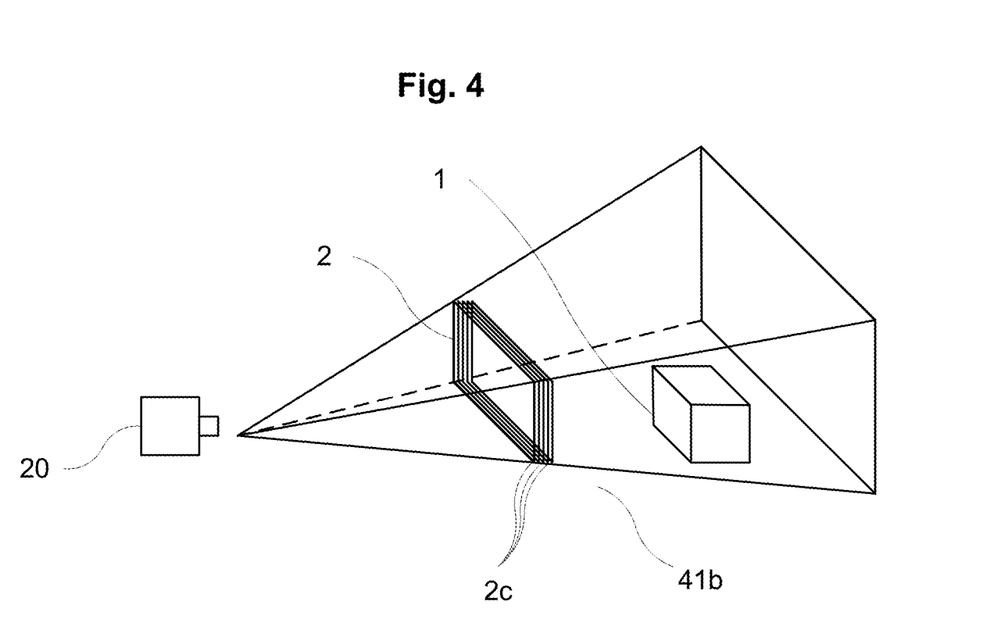
FIG. 4 is a diagram for explaining the operating principal of a multifocal image device.

FIG. 4 is another simplified view, also being similar to FIG. 1, and showing the case where a display device 41*b* is arranged to display a multifocal projection image, in turn comprising, or being selected from a set of, more than two, such as at least ten, different images 2*c* being rendered in parallel but with different focal planes in relation to the eye of the observing user. Hence, the images 2*c* may all be rendered in parallel by a rendering function, whereafter one of the rendered images 2*c* are shown depending on, for instance, a detected current focus distance of the user's eye. It is realized that such a multifocal display is only one of several possible examples where one single display may be arranged to display one or several of a possible set of rendered images 2*c*. In FIG. 4, the plurality of images are shown at the position of the viewport 2 but with an offset with respect to depth. In reality, the images 2*c* are projected to be displayed at the same place in space. Also, a screen display of the device 41*b* may be arranged at the shown viewport 2.

It is noted that both FIGS. 3 and 4 are very schematic, illustrating relevant principles pertaining to respective device 41*a*, 41*b*. The purpose of this is to illustrate the differences between different types of display devices with which the present invention is useful. In practise, the illustrated setups may, of course, be varied. For instance, a stereoscopic display device may also be a multifocal display device.

Figure 5:
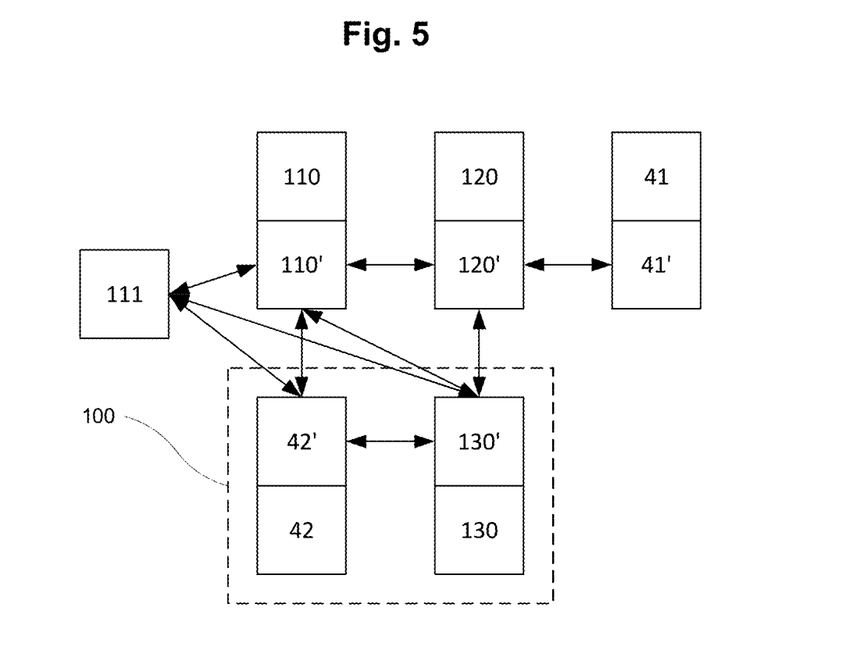
FIG. 5 is a diagram showing a system according to the present invention.

FIG. 5 illustrates a system 100 according to the present invention, for determining a current gaze direction of a user in relation to a three-dimensional ("3D") scene 10, the 3D scene 10 being sampled by a rendering function 110 to produce at least one projection image of the 3D scene 10.

FIG. 5 illustrates, using arrows, possible communication paths, all of which may not be provided or used in all embodiments.

It is realized that, in some embodiments, the system 100 comprises the rendering function 110, while in other embodiments the rendering function is an external part lying outside of the system 100.

The rendering function 110 may be implemented as a piece of computer software, such as a graphical computer game or other interactive computer application, or as a part of a larger piece of computer software such as an XR runtime for instance. The rendering function may have various interfaces 110' for communicating with other system 100 internal or system 100 external parts, such as the gaze direction detection means 130 described below and a logic module 111 arranged to control logic of a game, a GUI or similar. The particular topology or architecture shown in FIG. 5 is merely an example for illustrative purposes. For instance, in some embodiments the rendering function 110 may be partly or in full implemented as a remote service, such as a cloud service, feeding the finally rendered projection image to the display device 41 via the internet, such as via a wifi or 5G wireless internet connection.

As used herein, the term "interface" is intended to cover any suitably used logical, electric and/or physical interface, including wireless or cable communication interfaces and APIs (Application Programming Interfaces). Each illustrated such interface in FIG. 5 may comprise one or several distinct interfaces for various types of communication, for communication with various other entities and/or for communication of various different types of information, including one or more communication layers.

FIG. 5 further illustrates a reprojection means 120, arranged to communicate with the rendering function 110 via said interface(s) 110' and an interface 120' of the reprojection means 120. The reprojection means 120 is arranged to determine a reprojection transformation to be applied to the projection image before being displayed by the display device 41 so as to be visible to the user at a particular gaze time point, such as at each gaze time point. The reprojection means 120 may be a physically and/or locally standalone part, or may be a part of the display device 41. The determination of the reprojection transformation may be achieved using an algorithm implemented in hardware and/or software.

The reprojection means 120 may be implemented in software and/or hardware, using a suitable reprojection algorithm or circuitry, or a combination of these.

A "gaze time point" is a point in time when the projection image is visually displayed to the user. At this point, there will be a most updated gaze direction that has been determined before or at the gaze time point. Generally, at the gaze time point the rendering and reprojection have already been performed. However, the last determination of the (non-modified) gaze direction may have taken place before or after a rendering of a currently used projection image is finalized; and also before or after the reprojection transformation is applied.

As will be exemplified below, a possible effect of the reprojection is that a particular detected gaze direction being detected in relation to a display device 42 will translate into a different gaze direction in relation to a rendered scene 10 being shown, in the form of a projection image, on or by the display device 42. A modified gaze direction may be determined so as to be able to correctly translate the detected gaze direction in relation to the display device 42 into a corresponding gaze direction in relation to the scene 10 even after the reprojection has been executed.

In general, the reprojection transformation may be determined based on one or several of a number of pieces of information available to the reprojection means 120.

A first example of such a piece of information is a set of at least one known static or dynamically variable property of a physical display means, such as the display device 41, 41*b* or 41*c*, arranged to display said projection image.

A second example of such a piece of information is a detected movement of said physical display means.

A third example of such a piece of information is a detected movement of the user in relation to said physical display means.

A fourth example of such a piece of information is an externally provided trigger, such as provided by the rendering function 110 or a piece of hardware upstream of the reprojection means 120.

More concretely, the reprojection transformation may be of several different types, that may be applied one by one or in any combination, as the case may be. The reprojection transformation may be determined based on a priori knowledge of certain static or dynamically variable properties of the display device 41 and/or based on a detected absolute movement of the display device 41 and/or based on a detected movement of the display device 41 in relation to the user and/or an external trigger, such as the detection of missed image frames, for instance as a result of GPU bottlenecks.

Said "static or dynamically variable properties" may, for instance, be static or dynamically variable optical properties of lenses and/or projection surfaces used by the display device 41 in question.

In a first example, the reprojection transformation comprises a translation of the projection image and/or a rotation of the projection image and/or a rescaling of the projection image and/or a warping of the projection image.

As used herein, the term "warping" refers to a non-linear geometric transformation of a projection image, while a "reprojection" that refers to any transformation of a projection image including the production of an additional projection image (such as using interpolation techniques) based on one or several known projection images.

A translation, rotation or rescaling may be due to the detection of a movement of the display device 41, such as if the user wearing a head-mounted AR (Augmented Reality) or VR (Virtual Reality) display moves in a translational and/or rotational manner (side-to-side movements may correspond to a translation reprojection, whereas forward movements may correspond to a zoom-in rescale reprojection). A warping of the projection image may be due to non-linear lens properties in combination with a translational/rotational/rescale reprojection, and/or may be due to adapting the displayed image to a presently used display screen, taking into consideration non-linear lens or display properties, or similar.

In a second example, the reprojection transformation results in a synthetically determined intermediate image, produced by interpolation from one or several existing images. This may, for instance, be the case if missed image frames are detected, or for instance if an increased frame rate is desired due to, for instance, rapidly changing graphics.

In a third example, namely in the case in which the 3D scene 10 is sampled by the rendering function 110 to produce at least two projection images of the 3D scene 10 representing each image in a stereoscopic view arranged to be displayed in an AR/VR device 41*a* such as the one explained in connection to FIG. 3, the reprojection transformation may be determined for each of said images based on one or several static and/or dynamically variable properties of the AR/VR device 41*a* in question. In this case, the reprojection transformation may typically be slightly different between the two projected and displayed images.

In a fourth example, namely in the case in which the 3D scene 10 is sampled by the rendering function 110 to produce at least two projection images of the 3D scene 10 representing several alternative or supplementary images to be displayed on one and the same multi-image display 41*b*, such as the one explained in connection to FIG. 4, the reprojection transformation may be determined for each of said images based on at least one static and/or dynamically variable property of the multi-image display 41b in question.

Hence, the reprojection means 120 is arranged to receive each rendered image from the rendering function 110, once it is finally rendered by the rendering function 110. Preferably, there is no direct or indirect feedback from the reprojection means 120 back to the rendering function 110, preferably not even via the logic module 111. Instead, the reprojection means 120 preferably determines the reprojection transformation, applies the reprojection transformation to the rendered image and then passes it on to the display device 41, such as via a suitable interface 120' of the reprojection means 120 and a suitable interface 41' of the display device 41 (or via an internal interface, if the reprojection means 120 is an integrated part of the display device 41). Normally, the rendering of the image is much more GPU labour intensive than applying the reprojection transformation, and therefore applying the reprojection transformation to the already rendered image is more efficient and provides less latency than taking the reprojection transformation into account to re-render the image.

Furthermore, according to the present invention the system 100 comprises said gaze direction detection means 42. The gaze direction detection means 42 may be as described above, and is specifically arranged to determine a physical gaze direction of the user at a particular gaze time point. In general, the gaze direction detection may involve a "hit testing" algorithm, arranged to determine an object or area of interest, or similar, corresponding to a detected gaze direction.

As is the case for the reprojection means 120, the gaze detection means 42 may be implemented in software and/or hardware, using a suitable reprojection algorithm or circuitry, or a combination of these. Normally, the gaze detection means 42 will comprise or have access to some kind of hardware sensor, such as a visual sensor in the form of a camera, detecting the gaze direction of the user's eye.

At this point, the user the gaze direction of which is detected may wear the display device 41, 41a, 41b as a head-mounted display or may look at the currently projection image in some other way. The gaze direction is determined in relation to the scene 10.

The gaze direction detection means 42 may be a logically and/or physically standalone device, separated from the rest of the system 100 and/or the rendering function 110 but able to communicate with said parts via suitable Interfaces 42' of the gaze direction detection means 42. Specifically, the gaze direction detection means 42 may be arranged to communicate directly with the rendering function 110, via interfaces 42', 110', and/or with the logic module 111, via interface 42', as the case may be, in order to provide information directly or indirectly to the logic module 111 and/or to the rendering function 110 regarding a current gaze of the user in relation to the scene 10. Such information may then be used by the logic module 111 and/or the rendering function 110 to affect the appearance, structure and/or rendering of the scene 10. One example is that the detected current gaze direction may affect user interactable objects in the scene 10 as discussed above.

The system 100 further comprises a modified gaze direction detecting means 130, that may be an integrated part of the gaze direction detection means 42 or a logically and/or physically separated entity. The modified gaze direction detection means 130 may be arranged to communicate, via interfaces 130' and 120', with the reprojection means 120.

As is the case with the gaze direction detection means 42, the modified gaze direction detection means 130 may be implemented in software and/or hardware, using a suitable reprojection algorithm or circuitry, or a combination of these.

In particular, the modified gaze direction detection means 130 is arranged to receive information regarding said reprojection transformation that is applied to the projection image before the projection image is displayed on the display device 41 so as to be visible at said gaze time point. Such received information may be the reprojection transformation itself, or other information sufficient to determine properties of the reprojection transformation necessary to be able to determine a gaze direction in relation to the scene 10 based on a physical gaze direction in relation to the display device 41.

Furthermore, the modified gaze direction detection means 130 is arranged to determine a modified gaze direction of the user at said gaze time point, the modified gaze direction being determined in relation to the 3D scene 10 based on both said physical gaze direction and said reprojection transformation. In case the gaze direction means 42 is a different entity than the modified gaze direction detection means 130, information regarding said physical gaze direction may first be communicated from the gaze direction means 42 to the modified gaze direction detection means 130.

It is understood that the detected physical gaze direction may be a most recently detected physical gaze direction. This information may hence be provided from a detection lying a short time period in the past in relation to the gaze time point. Depending on the implementation of the gaze detection means 42, the detected physical gaze direction used by the modified gaze detection means may also be processed in various ways. For instance, if the gaze detection means 42 has determined that the user currently is gaze-following a particular object 1 of interest that moves across the screen, the detected physical gaze direction may be calculated based on a most recently detected gaze direction and using an extrapolation of a determined current movement of the gaze.

The modified gaze direction detection means 130 is then arranged to, for instance via interfaces 130' and 110', communicate the determined modified gaze direction of the user, or at least information regarding the determined modified gaze direction sufficient to determine the modified gaze direction, to the logic module 111 and/or the rendering function 110.

Figure 6:
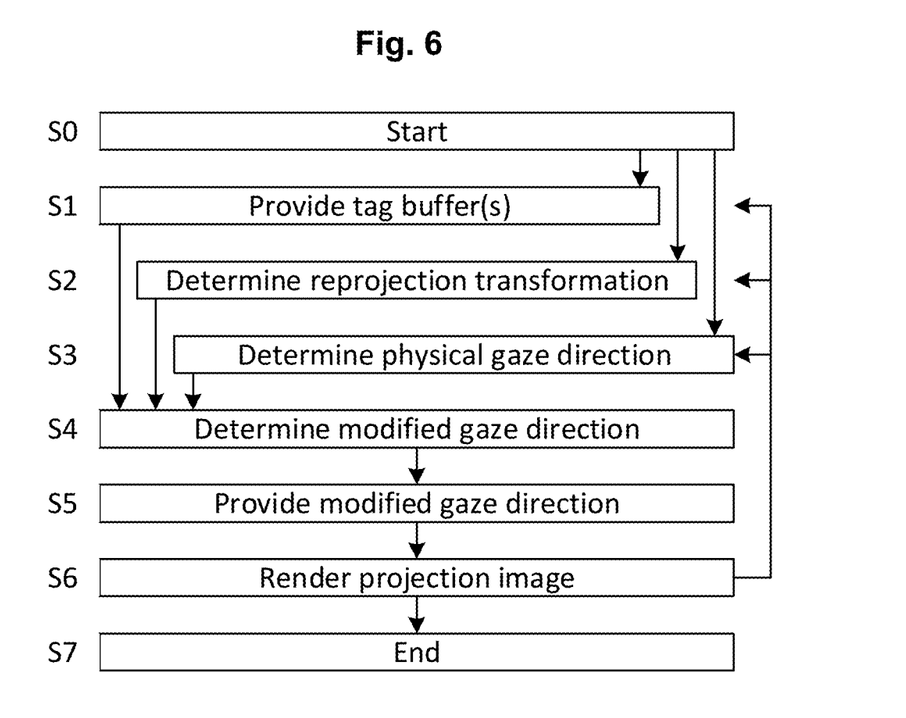
FIG. 6 is a flow chart illustrating a method according to the present invention.

FIG. 6 illustrates a method according to the present invention, for determining a current gaze direction of a user in relation to the 3D scene 10, the 3D scene 10 being sampled by the rendering function 110 to produce at least one 2D projection image of the 3D scene 10 (or, in an analogue manner, to produce a 3D projection hologram or similar of the 3D scene 10). As mentioned above, the 2D projection image is displayed on the display device 41, that may correspond to the viewport 2. As also mentioned, the sampling is performed based on, inter alia, the virtual camera 20 in turn being associated with at least a position of the virtual camera 20 and a direction of the virtual camera 20 in the 3D scene.

The method is performed by a system 100 of the type described above.

In a first step S0, the method starts.

In a subsequent step S2, the reprojection means 120 determines a reprojection transformation that has been, is, or is about to be, applied to the projection image before being displayed so as to be visible to the user at said gaze time point. This determination may be as described above.

In a step S3, that may be performed before, in parallel to or after step S2, the gaze direction detection means 42 determines a physical gaze direction of the user at said gaze time point. This determination may also be as described above. Hence, the determined physical gaze-direction at the gaze time point may be a most recently determined gaze direction, and to this most recently determined gaze direction gaze direction movement prediction algorithms may be applied in order to arrive at the "physical gaze-direction of the user a the gaze time point" in the present sense. Generally, steps S1-S3 may be performed in any order, but typically relate to one and the same gaze time point, in other words a point in time at which the gaze of the user falls onto a rendered and possibly reprojected transformed, visually displayed projection image.

In a subsequent step S4, a modified gaze direction of the user is determined at said gaze time point, the modified gaze direction being determined in relation to the 3D scene 10 based on both the physical gaze direction and the reprojection transformation. This determination may be as described above, and may be performed by the modified gaze direction detection means 130.

In a subsequent step S5, the modified gaze direction, or at least information regarding the modified gaze direction, may be provided to the logic module and/or to the rendering function 110 as described above.

In a subsequent step S6, the rendering function 110 may render a subsequent projection image based on said received modified gaze direction or said received information regarding the modified gaze direction. For instance, the rendering may then result in a different user interaction with a user interactable object; or the modified user gaze may result in the scene 10 changing in some other way.

Thereafter, the method may iterate, any of the steps S1 and forwards (and in particular steps S2-S6) being applied but at later gaze time points, and in relation to subsequently rendered projection images. As various events happen, such as a user moving about with a head-mounted display or frames being dropped, various reprojection transformations may be applied. Since the modified gaze direction detection means 130 is able to intercept, with low latency, information regarding such updated reprojection transformations, it is at all times possible for the modified gaze direction information to be provided to the logic module 111 and/or rendering function 110, again at low latency, for use when rendering updated projection images.

In a subsequent step S7, the method ends.

As mentioned, the reprojection means 120 may be an entity logically separate from the rendering function 110. As is also clear from the above description, the reprojection means 120 is arranged downstream, with respect to the chain of processing steps relating to the projection image before being displayed to the user, in relation to the rendering function 110. In other words, the already finally rendered image is provided by the rendering function 110 for use by the reprojection means 120 and to provide a reprojected image for actual display to the user.

As discussed above, the modified gaze direction may be determined by the modified gaze direction detection means 130, in turn being arranged to receive reprojection transformation information via a first interface 130' and to provide modified gaze direction information via a second interface 130' (the first and second interfaces possibly being one and the same), to the rendering function 110 and/or to the logic unit 111, the logic unit 111 for instance being a game controller.

In some embodiments, the gaze direction detection means 42 will use tag buffers to determine the gaze direction at the gaze time point. This may also be expressed such that the rendering function 110 as a result of the rendering projects the virtual world (the scene 10) to a set of at least one tag buffers (one of which may be a colour bitmap of the above type).

For instance, such a tag buffer can be a depth tag buffer, comprising information regarding a respective virtual distance to each of various points in the scene 10 from the virtual camera 20. Another example is a user interactibility tag buffer, comprising information regarding objects that are (or are not) user interactable. Normally, such a tag buffer comprises or represents a bitmap associating each pixel in the projection image (or a corresponding projection of the scene 10) with a particular property or set of properties. Such tag buffers may, for instance, be used to increase computational efficiency and/or to decrease latency. Tag buffer information may be provided to the gaze direction detection means 42 by the logic module 111 and/or the rendering function 110.

In some embodiments, and as is illustrated in FIG. 6, the method further comprises, in step S1, determining, and providing to the modified gaze direction detection means 130, a set of at least one tag buffer in relation to the 3D scene 10. That the tag buffer is "in relation to the 3D scene" means that the tag buffer is a tag buffer that maps onto the 3D scene via a suitable projection, such as said projection image. The mapping may be 1:1 in terms of pixels, but may also be rescaled, warped or modified in some other way with respect to pixel coordinates.

Then, the modified gaze direction detection means 130 may determine, as a part of the present method, said modified gaze direction further based on said set of at least one tag buffer, for instance as generally exemplified above. In particular, such a tag buffer may be updated based on the reprojection in question for determining the modified gaze direction. For instance, a tag buffer may be reprojected to handle missed frames, by suitable interpolation.

As also mentioned above, the set of at least one tag buffer may be determined and provided by said logic unit 111 and/or by the rendering function 110. This may depend on the type of tag buffer and their purpose.

As discussed above, the gaze direction may be defined in different ways, such as a gaze angle; an area of interest towards which the user's gaze is directed; or a particular object of interest towards which the user's gaze is directed. In particular in the last case, the modified gaze direction may comprise information regarding a particular object 1 in the 3D scene 10 the projection of which is present along the detected gaze direction in the projection image. Then, both the determination of the modified gaze direction and the identifying of said object 1 may be performed without the rendering function 110 (and possibly also not the logic module 111) obtaining direct information regarding the said modified gaze direction. Hence, in this case the modified gaze direction means 130 may perform the determination of the modified gaze direction to produce an object or area of interest corresponding to the determined gaze direction as modified using the reprojection transformation. This determination may then result in that a same object of interest as was pinpointed by the detected gaze direction is also pinpointed as an object of interest according to the modified gaze direction, or a different object. It is noted that, in this case, the modified gaze direction detection means 130 has access to, and uses, information regarding one or several objects 1 in the 3D scene 10. Such information may be provided to the modified gaze direction detection means 130 at least partly in the form of a corresponding tag buffer. Then, the modified gaze direction detection means 130 may provide updated information regarding the determined object or area of interest, with consideration taken to the reprojection transformation, to the logic module 111 and/or the rendering function 110 for use therein, such as for determining a particular user interaction with that object 1 or area of interest.

In some embodiments, tag buffer information may be modified in the present method as a result of a detected reprojection transformation. For instance, the modified gaze direction detection means 130 may perform such a modification of a received tag buffer before or as a part of the determination of the modified gaze direction. Generally, the present method may comprise a step in which at least one tag buffer is modified based on the detected reprojection transformation before the determination of the modified gaze direction.

Based on tag buffer information thus modified, in some embodiments an identity of a gaze-interactable zone or object that is currently gazed at by the user may then be determined.

For instance, the modified gaze direction may be determined, by the modified gaze direction detection means 130, based at least partly on a parallax effect due to said reprojection transformation. This may then involve the modified gaze direction detection means 130 either using a depth tag buffer to determine a parallax effect of a detected translational reprojection transformation, this parallax effect in turn being used when determining the modified gaze direction. Alternatively or supplementary, the modified gaze direction detection means 130 may first modify the received depth tag buffer to reflect or correspond to a detected reprojection transformation that has a parallax effect, and then use that modified depth tag buffer to determine the modified gaze direction.

Such parallax effects may have considerable effects, for instance if an object of interest located further away from the virtual camera 20 than a closer obscuring object pops into or out of vision for the user as a result of a translational movement detected and used as a reprojection transformation before displaying the rendered image. Even the movement of the user's pupils as a result of the user directing her gaze in a different direction may in some cases suffice to achieve such a parallax effect.

It is understood that, in this and in other examples, the reprojection transformation may involve a linear or non-linear amendment to the image where, for instance, objects 1 located further away from the virtual camera 20 are translated less in the projection image than images located closer to the virtual camera 20, and that the reprojection transformation itself may involve moving individual objects more or less into or out of sight behind closer located, obscuring objects.

The present invention has so far been described in terms of the system 100 and the present method. It is understood, however, that the present invention also relates to a computer software function for determining a current gaze direction of a user in relation to a three-dimensional scene 10 of the above discussed type. Such a computer software function is configured to, when executed on suitable physical and/or virtual computer hardware, perform at least some of the above-described method steps.

In particular, said computer software function is arranged to, when thus executed, determine or receive (such as via a suitable interface as described above) said physical gaze direction (or information regarding said physical gaze direction) of the user at said gaze time point; to receive (such as via a suitable interface as described above) said reprojection transformation (or information regarding said reprojection transformation) to be applied to the projection image before being displayed so as to be visible to the user at a gaze time point; and to determine said modified gaze direction of the user in relation to the 3D scene 10 at said gaze time point in the above-discussed manner, based on both said physical gaze direction (information) and said reprojection transformation (information).

In some embodiments, the computer software function is arranged to be executed on hardware of the gaze direction detection means 42 and/or the modified gaze direction detection means 130. In other embodiments, at least part of the calculations used for said determinations made by the computer software function is performed remotely, such as using a cloud service or similar. Then, communication may take part between, on the one hand, the gaze direction detection means 42 and/or the modified gaze direction detection means 130 and, on the other hand, parts of the computer software function performing such calculations remotely. Communications may take part over the internet, as is conventional as such.

Normally, the computer software function is a part of the system 100. In case the computer software function is executed at least partly remotely, the system 100 may hence be considered to also encompass such remote functionality, and possibly also associated remotely arranged hardware. In particular, in case some or all of the determination functionality of the gaze direction detection means 42 and/or the modified gaze direction detection means 130 is performed remotely by said computer software function, the gaze direction detection means 42 and/or the modified gaze direction detection means 130 may be considered to encompass such remote functionality, and possibly also such remote hardware, as the case may be.

Figure 7:
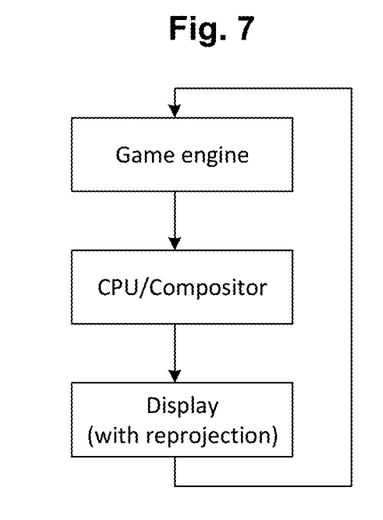
FIGS. 7 and 8 illustrate an example embodiment of the present invention.
Figure 8:
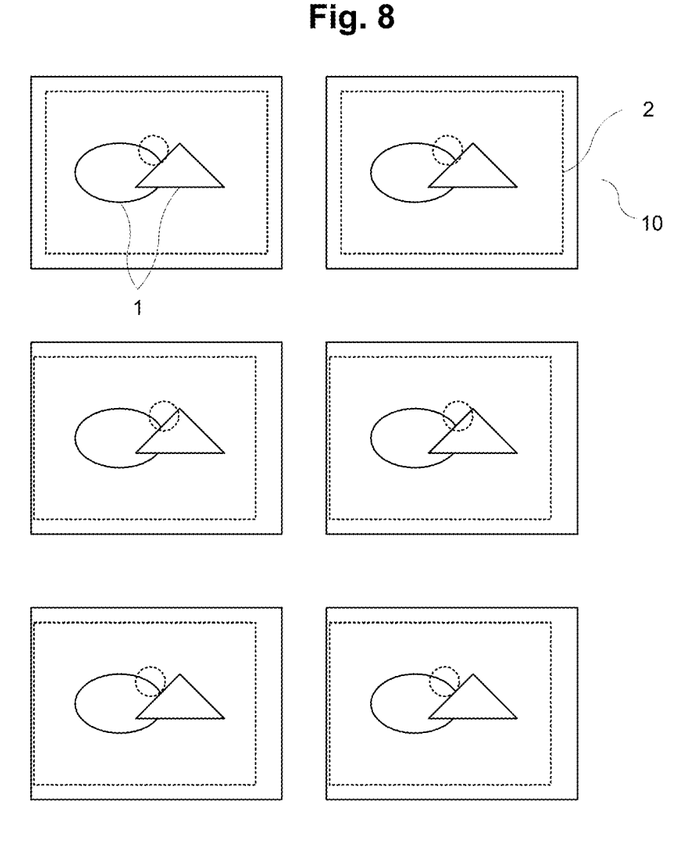

FIG. 7 illustrates (as a flowchart) a feedback loop, and FIG. 8 illustrates three pairs of reprojection images, FIGS. 7 and 8 together illustrating a simple example embodiment of the present invention where the reprojection transformation is a translation and where the display is a head-mounted stereoscopic AR/VR display.

As is illustrated in FIG. 7, the game engine (corresponding to the logic module 111) determines the geometric layout and features of the scene 10. This information is provided to the GPU/Compositor (corresponding to the rendering function 110), in turn producing two renditions in the form of the left/right projection image pair. These projection images are provided to the head-mounted display (corresponding to display device 41*a*) as a stereoscopic pair of images. The display comprises functionality for reprojection, based on detected movements the user performs that affect the translational and/or rotational position of the head-mounted display in question. Such movement detection may take place using, for instance, a conventional MEMS circuit embedded in the head-mounted display unit. The display also comprises functionality for gaze detection (corresponding to the gaze direction detection means 42) and for adjusting the detected gaze direction based on a currently used reprojection (corresponding to the modified gaze direction detection means 130).

The top pair of images shown in FIG. 8 shows two objects 1 (an ellipse and a triangle) in a scene 10. The left image is presented to the left eye of the user by the stereoscopic display device; the right image is presented to the right eye of the user. The broken-lines rectangle represents the viewport 2 (the part of each image visible to the user). As can be seen from FIG. 8, the compositor renders the projection image with a certain margin around the viewport 2, so as to be able to apply translational reprojections without any re-rendering work being required. The broken-lines circle represents a detected gaze direction (that may be used to determine a current object or area of interest, such as for user interaction).

In the second-from-top pair of images shown in FIG. 8, the user has moved her head about 2° to the left (as compared to the predicted head position when the rendering was initiated by the game engine), resulting in a corresponding translational reprojection moving the viewport 2 correspondingly to the left. It is noted that a detected physical translation to the left of the user's head could have resulted in a similar reprojection. The gaze tracker has at this point no knowledge about the applied reprojection transformation.

The reprojection will occur after the rendering, such as between 10 and 50 ms into the future in relation to the rendering. At this point, the game engine is not aware of the projection image translations. Generally, the game engine is not aware of any projection image corrections that are applied late in the rendering pipeline, compositor or runtime-based, on updated sensor readings from, for instance, a head-mounted display on position and directions of the displays.

As the user turns her head to the left, she follows the object of interest (in the example shown the upper right part of the ellipse 1) with her eyes. The result is that the gaze tracker detects an updated gaze direction, due to the user following the object of interest with her eyes as she turns her head to the left. To the gaze tracker's point of view, this gaze movement appears to be a steady drift to the right in the images, resulting in a detection of the current gaze direction as illustrated in the second-from-top pair of images in FIG. 8. It is noted that the detected object of interest may now, erroneously, be interpreted as part of the triangle.

Then, the gaze tracker (or in fact the modified gaze direction detection means) takes the applied reprojection transformation into consideration, and modifies the detected gaze direction correspondingly. For instance, this may be or comprise the application of the same transformation as the reprojection transformation in question, in this case a translation to the left. The result is shown in the bottom pair of images, where the object of interest is again the top-right part of the ellipse.

It is then this updated gaze direction information (such as a determined object or area of interest) that is fed back from the display to the game engine. The result is that the game engine (such as an XR runtime) is provided with correct information regarding the current gaze direction. For instance, the game controller will know what was actually shown to the user, and can then compute what the user was looking at in the previous frame (so that a running application or subsystem can accurately understand what was being focused on by the user).

As a result, the eye tracker of the display determines that as the head turns to the left, the gaze in relation the head goes in the right direction, if gaze is fixed on the object of interest. If the game engine does not take into account that the head moves to the left, the game engine will think that the gaze is in a smooth pursuit right from the object of interest. Thus, the position of the object of interest, in relation the head direction of the user, has to be adjusted continuously.

Above, preferred embodiments have been described. However, it is apparent to the skilled person that many modifications can be made to the disclosed embodiments without departing from the basic idea of the invention.

For instance, the method described above may comprise many additional features, apart from the ones described herein, such as built-in user interaction functionality.

The use of the determined current user gaze direction can vary. For instance, a possible use is for locally increasing a 2D sampled image quality in the vicinity of a currently focussed zone of the screen 41, in order to prioritize computer resources for providing a more high quality user experience from a computer graphics point of view.

A computer software function according to the invention may also be an integrated part of a computer game or any other complex computer software function. It may also be installed on a gaze direction detection means such as the means 42 disclosed in FIG. 2.

In general, all which has been said herein regarding the method is equally applicable to the said system and computer software function, and vice versa.

Hence, the invention is not limited to the described embodiments, but can be varied within the scope of the enclosed claims.

What is claimed is:

1. A method in a system for determining a current gaze direction of a user in relation to a three-dimensional ("3D") scene, the 3D scene being sampled by a rendering function executed on a graphic processing unit (GPU) to produce at least one projection image of the 3D scene, wherein the method comprises the steps:

determining, by a reprojection means executed on a central processing unit (CPU), a reprojection transformation to be applied to the projection image before the projection image being visibly displayed to the user at a gaze time point;

determining, by a gaze direction detection means executed by an eye-tracking device, a gaze direction of the user at said gaze time point;

determining, by a modified gaze direction detection means executed on the CPU, a modified gaze direction of the user at said gaze time point, the modified gaze direction being determined in relation to the 3D scene based on both the user's gaze direction and the reprojection transformation and setting, by the modified gaze direction detection means, a current gaze direction in relation to the 3D scene as the modified gaze direction of the user.

2. Method according to claim 1, further comprising:

reprojecting the projection image separately from said rendering function after the 3D scene sampled by said rendering function.

3. Method according to claim 1, wherein the reprojection transformation is determined based on at least one of a set of at least one known property of a physical display means, such as a display screen, arranged to display said projection image;

a detected movement of said physical display means; and a detected movement of the user in relation to said physical display means.

4. Method according to claim 1, wherein the modified gaze direction is determined by a modified gaze direction detection means, arranged to receive reprojection transformation information, via a first interface, and to provide modified gaze direction information, via a second interface, to a logic unit.

5. Method according to claim 4, wherein the method further comprises determining, and providing to the modified gaze direction detection means, at least one tag buffer in relation to the 3D scene;
the modified gaze direction detection means determining said modified gaze direction further based on said at least one tag buffer.

6. Method according to claim 5, wherein
said at least one tag buffer is determined and provided by said logic unit.

7. Method according to claim 5, wherein
the modified gaze direction detection means receives information regarding an object in said 3D scene at least partly in the form of a corresponding tag buffer.

8. Method according to claim 7, wherein
both the determination of the modified gaze direction and an identification of said object are performed without the rendering function obtaining direct information regarding the said modified gaze direction.

9. Method according to claim 5, wherein the method further comprises modifying said at least one tag buffer based on said reprojection transformation before determining the modified gaze direction.

10. Method according to claim 5, further comprising:
determining, by the modified gaze direction detection means, the modified gaze direction is determined based at least partly on a parallax effect due to said reprojection transformation.

11. Method according to claim 1, wherein
the reprojection transformation comprises at least one of the following: a translation of the projection image, a rotation of the projection image, a rescaling of the projection image, a warping of the projection image, wherein
the reprojection transformation results in a synthetically determined intermediate image, produced by interpolation from one or several existing images.

12. Method according to claim 1, wherein
the 3D scene is sampled by the rendering function to produce at least two projection images of the 3D scene representing each image in a stereoscopic view arranged to be displayed in an AR (Augmented Reality)/VR (Virtual Reality) device, and wherein
the reprojection transformation is determined for each of said images based on a property of the AR/VR device in question.

13. Method according to claim 1, wherein
the 3D scene is sampled by the rendering function to produce at least two projection images of the 3D scene representing several alternative or supplementary images to be displayed on a multi-image display, and wherein
the reprojection transformation is determined for each of said images based on a property of the multi-image display in question.

14. A system for determining a current gaze direction of a user in relation in relation to a three-dimensional ("3D") scene, the 3D scene being sampled by a rendering function executed on a graphic processing unit (GPU) to produce at least one projection image of the 3D scene, the system comprising:
a gaze direction detection means executed by an eye-tracking device, the gaze direction detection means arranged to determine a gaze direction of the user at said gaze time point;
a modified gaze direction detecting means comprising a central processing unit (CPU), the modified gaze direction detection means arranged to receive information regarding a reprojection transformation applied to the projection image before the projection image is visibly displayed to the user at said gaze time point, and further arranged to determine a modified gaze direction of the user at said gaze time point, the modified gaze direction being determined in relation to the 3D scene based on both said user's gaze direction and said reprojection transformation, and
wherein a current gaze direction of the user in relation to the 3D scene is set by the modified gaze direction detection means based on the modified gaze direction.

15. A non-transitory computer readable medium comprising computer readable instructions that, when executed by a processor, cause the processor to perform the operations for determining a current gaze direction of a user in relation to a three-dimensional ("3D") scene, the 3D scene being sampled by a rendering function executed on a graphics processing unit (GPU) to produce at least one projection image of the 3D scene, wherein the operations including the steps:
determine or receive, by a gaze direction detection means executed by an eye-tracking device, a gaze direction of the user at said gaze time point;
receive, a modified gaze direction detecting means comprising a central processing unit (CPU), information regarding a reprojection transformation applied to the projection image before the projection image is visibly displayed to the user at said gaze time point;
determine, by the CPU, a modified gaze direction of the user at said gaze time point, the modified gaze direction being determined in relation to the 3D scene based on both the user's gaze direction and the reprojection transformation and
set, by the modified gaze direction detection means, a current gaze direction in relation to the 3D scene as the modified gaze direction of the user.

* * * * *